United States Patent
Ulutas et al.

(10) Patent No.: US 12,392,764 B2
(45) Date of Patent: Aug. 19, 2025

(54) DIELECTRIC LOSS, GLASS TRANSITION TEMPERATURE, AND BRITTLENESS OF MODIFIED BITUMEN

(71) Applicant: YILDIZ TEKNIK UNIVERSITESI, Istanbul (TR)

(72) Inventors: Hulusi Kemal Ulutas, Istanbul (TR); Huseyin Deligoz, Istanbul (TR); Deniz Ulutas, Istanbul (TR); Mustafa Sinan Yardim, Istanbul (TR); Sahin Yakut, Istanbul (TR); Deniz Bozoglu Parto, Istanbul (TR); Betul Deger Sitilbay, Istanbul (TR)

(73) Assignee: YILDIZ TEKNIK UNIVERSITESI, Istanbul (TR)

( * ) Notice: Subject to any disclaimer, the term of this patent is extended or adjusted under 35 U.S.C. 154(b) by 140 days.

(21) Appl. No.: 18/284,882

(22) PCT Filed: Mar. 11, 2022

(86) PCT No.: PCT/TR2022/050221
§ 371 (c)(1),
(2) Date: Sep. 29, 2023

(87) PCT Pub. No.: WO2022/211759
PCT Pub. Date: Oct. 6, 2022

(65) Prior Publication Data
US 2024/0183840 A1    Jun. 6, 2024

(30) Foreign Application Priority Data

Mar. 29, 2021 (TR) ............... 2021/005614

(51) Int. Cl.
*G01N 33/42* (2006.01)

(52) U.S. Cl.
CPC .................................. *G01N 33/42* (2013.01)

(58) Field of Classification Search
CPC ...................................................... G01N 33/42
See application file for complete search history.

(56) References Cited

U.S. PATENT DOCUMENTS 3,349,051 A    10/1967 Alexander et al.
2017/0323700 A1*  11/2017 Ryan .................. H01B 3/28

OTHER PUBLICATIONS

Tugce Kara, Dielectric Properties of Asphalt Materials, Istanbul University, Institute of Graduate Studies in Sciences Department of Physics, M.Sc Thesis, 2019, pp. 1-56.
Feng Chen, et al., A study on dielectric response of bitumen in the low-frequency range, Road Materials and Pavement Design, 2015, pp. 153-169, vol. 16, No. S1.

(Continued)

*Primary Examiner* — Alesa Allgood
(74) *Attorney, Agent, or Firm* — Bayramoglu Law Offices LLC (57) ABSTRACT

A determination of dielectric loss, glass transition temperature, and brittleness of modified bitumen is provided. Bitumen modified with 5% polyester resin can still maintain its flexible structure at temperatures approximately 10° C. lower compared to pure bitumen and this modified bitumen can be used in regions where temperature differences are high.

13 Claims, 8 Drawing Sheets

(56) References Cited

OTHER PUBLICATIONS

C. Borsellino, et al., Effects of powder concentration and type of resin on the performance of marble composite structures, Construction and Building Materials, 2009, pp. 1915-1921, vol. 23.

Murat Okubay, Investigation of Marble Waste Usage As Aggregate In Bituminous Hot Mixtures, 2016, pp. 1-178, Yildiz Technical University—Graduate School Of Natural And Applied Sciences.

* cited by examiner

DIELECTRIC LOSS, GLASS TRANSITION TEMPERATURE, AND BRITTLENESS OF MODIFIED BITUMEN

CROSS REFERENCE TO THE RELATED APPLICATIONS

This application is the national phase entry of International Application No. PCT/TR2022/050221, filed on Mar. 11, 2022, which is based upon and claims priority to Turkish Patent Application No. 2021/005614, filed on Mar. 29, 2021, the entire contents of which are incorporated herein by reference.

TECHNICAL FIELD

The invention relates to the determination that bitumen modified with 5% Polyester Resin can still maintain its flexible structure at temperatures approximately 10° C. lower compared to pure bitumen and that this modified bitumen can be used in regions where temperature differences are high.

BACKGROUND

Meeting the transportation needs of people is one of the primary responsibilities of service providers. The transportation industry is also the necessary structure to meet these needs. Advanced road networks are obtained as a result of large investments in this industry. Therefore, it is possible to say that every innovative study and contribution made in this field will also be of great benefit to the country's economy. Transportation investments have always required great expenditures in Turkey in the past, present, and future time and will continue to do so. It cannot be ignored that the existing roads also have constantly costly needs while there are a lot of transportation projects planned to be carried out. Minimizing the cost-requiring situations of the roads so far in transportation investments will both minimize resource consumption and pave the way for new investments for this reason.

The lifespan of road surfaces is not infinite as is known. Even roads with the best pavement surface wear out and deteriorate over time. These deteriorations are caused by many factors such as increasing population and accompanying heavy traffic factors, environmental conditions and the variability of these conditions in Turkey, limited resources, and material.

One of the most important indicators of the development of countries is their transportation networks. The features of the transportation networks also show the quality of the service provided in the current situation. It is very important to choose the appropriate type of material considering the traffic loads and environmental conditions so that the roads can show the expected performance throughout their service life. Road pavements are the visible part of the road, and the problems in these parts can often be detected from the surface condition. Especially these are the superstructure elements to be considered since they are the contact surfaces between the road and vehicles on it. Many deterioration situations emerge over time in bituminous pavements, which are the most commonly used road superstructure type in Turkey. Therefore, it is important to improve the bitumen properties that bind the pavement and to make performance evaluations from different angles.

Bitumen is a highly skilled material that has been used in engineering studies for thousands of years and can assume important tasks according to its intended use. It is known that refined bitumen was first produced in a crude oil refinery in the United States in the early 1900s.[1]

After this date, the use of bitumen has gradually increased worldwide and the use of bitumen has become a very important application, especially in road construction. It was stated in a study conducted in 2011 that the current consumption of bitumen worldwide is approximately 102 million tons per year and 85% of this amount is used in road pavements.[2]

Therefore, it is obvious that improving the engineering properties of bitumen will provide significant benefits to the industry. Bituminous pavements are expected to be superior in performance. If bituminous binders are used alone as binders in road pavements, many problems such as an increase in crude oil prices, increase in traffic load, deformations, high maintenance-repair costs, and shortened service life are encountered. There is a need to increase the strength of and improve the performance of bituminous binders to solve these problems.

The structural properties of bitumen material, which is used in the structure of asphalt, which we frequently use in our daily lives, especially in the transportation industry, and whose task is to ensure that stone components called aggregates stick together, are very important. Because preserving the structure of bitumen will cause the asphalt to preserve its structure without scattering. Asphalt roads deteriorate, crack, and collapse in a short time as a result of horizontal and vertical stresses caused by temperature differences between seasons in Turkey, where all seasons are seen, highway preference, excessive vehicles with heavy wheel load. In addition, cracks occur due to freezing-thawing, especially in winter seasons, in regions where day and night temperature differences are high. These deteriorations and cracks disrupt the structure of the road and pose a significant risk to driving safety. Therefore, the bituminous pavement needs to be renewed frequently.

If bituminous binders are used alone as binders in road pavements, many problems such as an increase in crude oil prices, increase in traffic load, deformations, high maintenance-repair costs, and shortened service life are encountered.

There is a need to increase the strength of and improve the performance of bituminous binders to solve these problems.

SUMMARY

The object of the present invention is to determine the modified bitumen that can still maintain its flexible structure at lower temperatures compared to the pure bitumen being used and that can be used in regions where temperature differences are high and temperatures in the winter seasons are very low due to this feature. 5% Polyester Resin modified bitumen was produced for this purpose and it was shown that it can be used at temperatures approximately 10° C. lower compared to pure bitumen.

BRIEF DESCRIPTION OF THE DRAWINGS

The graphics obtained in the method for achieving the objects of the present invention are shown in the accompanying figures.

These figures are as follows.

DETAILED DESCRIPTION OF THE EMBODIMENTS

Bitumen with AC 50-70 penetration was used as bitumen in the study of the invention.

The physical properties of the pure (non-modified) bitumen used are as follows:

The penetration value of bitumen was determined as 57.8 according to TS EN 1426 standard. This value corresponds to the bitumen class with 50-70 penetration.

The specific gravity value of the bitumen was determined according to TS EN 15326 standard and obtained as 1.081 gr/cm$^3$.

The flash point of bitumen was determined as 334° C. according to TS EN ISO 2592 standard.

The softening point of bitumen was determined as 49.1° C. according to TS EN 1427 standard.

The frass breaking point of the bitumen was determined as −10° C. according to TS EN 12593 standard.

The ductility value of the bitumen with force measurement was measured as 0.3629 j/cm$^2$ for a temperature of 10° C. according to TS EN 13589 standard.

The heating loss value of bitumen as a thin film (RTFOT) was determined as 0.14% according to TS EN 12607-1 standard. In addition, the penetration value obtained after RTFOT was measured as 36.8, the permanent penetration value was 63.7, and the softening point was 53.4° C.

The dynamic viscosity value of bitumen is 450 cP according to TS EN 13302 standard.

The percentage of elastic return of the bitumen is zero according to TS EN 13398.

The chemical properties of the pure (non-modified) bitumen used are as follows:

Bitumen mainly refers to the class of black or dark-colored (solid, semi-solid, or viscous) binders, consisting of natural or high molecular weight hydrocarbons, such as asphalt, tars, pitch, and asphaltites according to the International Society of American Testing and Materials (ASTM).

The structures that make up its chemistry are saturated aromatic, resin, and asphaltene compounds. There are five main elements in the chemical composition of bitumen: carbon, hydrogen, sulfur, oxygen, and nitrogen. Although the amounts of these elements in the bitumen content vary depending on the source of the bitumen, the conditions in the transportation and production process, are generally observed in the ranges of 82-88% carbon, 8-11% hydrogen, 0-6% sulfur, 0-1.5% oxygen and 0-1.0% nitrogen. Bitumen, which is coexistent with non-metallic derivatives and has adhesive properties, is completely dissolved in carbon disulfide ($CS2$).

Production of modified bitumen samples consists of the following steps:

Bitumen with AC 50-70 penetration is provided as asphalt cement,

Bituminous material with the above-mentioned properties, and Polyester Resin material is provided for the modification of pure (non-modified) bitumen, The temperature in the range of 160±10° C. is obtained, by operating the drying oven device to be used in the sample preparation processes (It is ensured in this way that the device reaches the desired temperature empty at least half an hour before the sample is placed. The non-modified bitumen, which is in the solid or semi-solid form at room temperature, is placed in the drying oven. All of the material is kept until it reaches the same temperature.)

The material is mixed by hand using a high-temperature resistant (non-deformable to 160±10° C.) mixer, and then the surface temperature is determined with the help of a temperature measurement device (thermometer) (this value is expected to be in the range of 160±10° C.), Firstly, the non-modified bitumen, which is in the solid or semi-solid form at room temperature, is kept in the drying oven, which is pre-set at 160° C., until all of the material reaches the same temperature (approximately 1 hour), The material is mixed with the help of a spatula to check that the appropriate temperature is provided homogeneously, and then the surface temperature is determined with the help of a laser thermometer, The bitumen reaching the appropriate temperature is taken into the mixing unit of the high-speed mixer device to be brought together with the additive material, The polyester resin, which is an additive stored in a glass container that does not come into contact with air at room temperature, is added to the mixing unit in an amount corresponding to 5% of the bitumen weight, (For example; adding 100 g of polyester resin to 2000 g of bitumen)

The device is set to rotate at 500 rpm and it is operated to obtain a mixture at a temperature of 160° C., The mixing process is continued (between approximately 20 and 30 minutes) until the additive material is evenly distributed over the entire bitumen used and becomes a homogeneous mixture, The modified polyester resin modified bitumen sample is filled into metal containers when the period is completed and it is kept at room temperature, Modified bitumen material is cooled to room temperature for testing, The modified mixture sample is heated in the drying oven and it is made measurable to determine the material properties by dielectric spectroscopy method, The modified material is mixed for a few minutes with the help of a spatula before using it, The material in different thicknesses (less than 5 mm thickness), is laid on a non-stick surface (oily paper) with the help of a spatula, 4 cm in diameter. Because, a sample with proper dimensions is required to determine the dielectric properties by dielectric spectroscopy (The sample is stored in a way that it will not be damaged until it reaches the laboratory where the dielectric properties will be analyzed.)

Thus, bitumen modified with 5% isophthalic acid-based isophthalic unsaturated polyester resin is produced.

Production of isophthalic acid-based isophthalic polyester resin is as follows:

Isophthalic acid-based isophthalic unsaturated polyester resins added to the bitumen were produced by undergoing condensation reaction of diol/polyols with dibasic acids and different product structures were formed according to the chemical structures of the starting materials used. Isophthalic-based SMC-BMC [Sheet Molding Compound/Bulk Molding Compound] is a polyester specially prepared for polyester and materials with excellent mechanical properties are obtained with this high viscous and reactive polymer. Unlike previous patents and studies, the polyester resin used is produced only from isophthalic, which is the isomer of phthalic acid, as the diacid structure. It is aimed to give strength and flexibility as well as hardness to asphalt with the use of isophthalic acid-based isophthalic unsaturated polyester only.

Dielectric investigation for pure bitumen and 5% isophthalic acid-based isophthalic unsaturated polyester resin modified bitumen (Calculation of glass transition temperature and durability values):

Dielectric spectroscopy measurements for pure and modified bitumen are also defined as capacitive measurements. Bitumen and modified bitumen were analyzed in form of capacitors with parallel plates by placing them between conductive electrodes.

The thicknesses of pure bitumen and 5% polyester resin (isophthalic acid-based isophthalic unsaturated polyester resin) modified bitumen were taken equally (2.5 mm) to see the effect of the modification.

Dielectric measurements were performed using a dielectric spectrometer under varying electric field in the frequency range of 0.1 Hz-20 MHz and the temperature range of −40° C. to +40° C. Capacities (C) and dielectric loss rates (tan δ) of pure and modified bitumen were measured. From these values, dielectric constant—ε', and dielectric loss—ε" were obtained. In addition, the electrical module—M" was calculated from the data.

Figure 4:
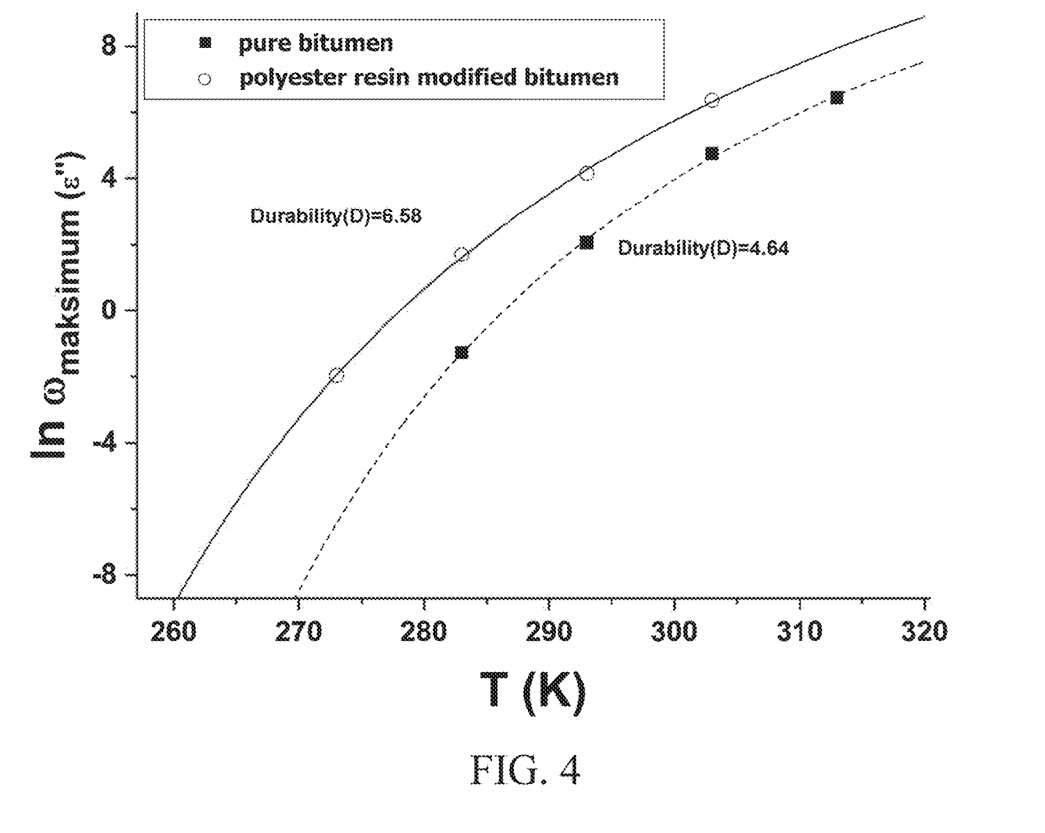
FIG. 4: Dependence of the electrical module M" on the angular frequency and the Cole-Cole slopes for pure bitumen.
Figure 5:
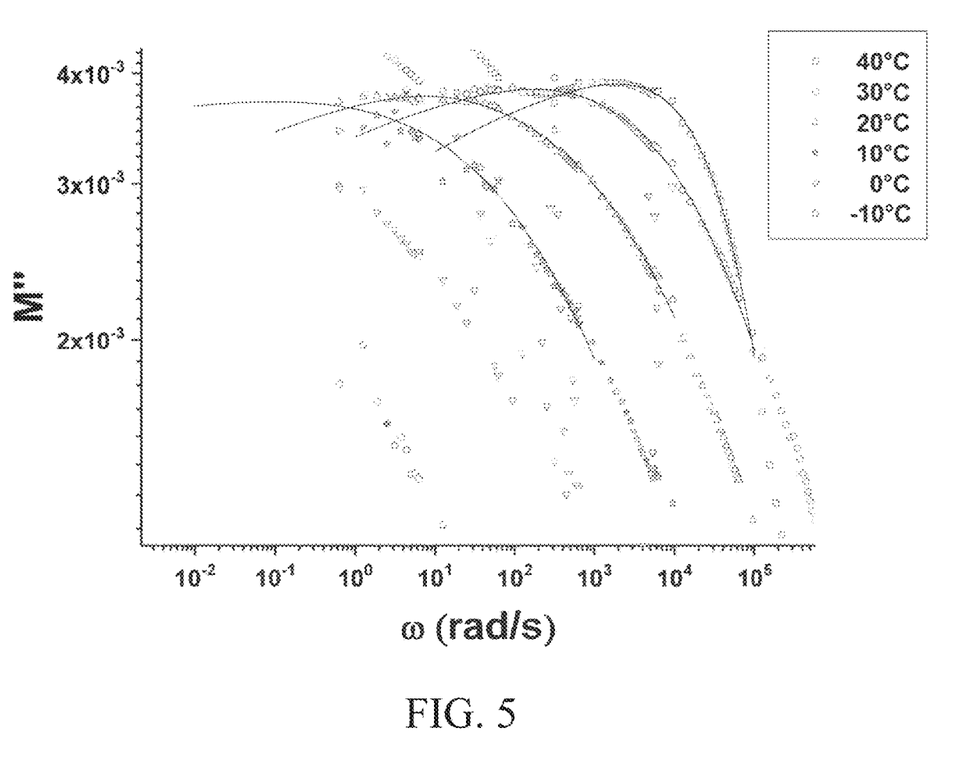
FIG. 5: Dependence of the electrical module M" on the angular frequency, and the Cole-Cole slopes for 5% isophthalic acid-based isophthalic unsaturated polyester resin modified bitumen.

FIG. 4 and FIG. 5 show the dependence of M" data on angular frequency for pure bitumen and 5% polyester resin (isophthalic acid-based isophthalic unsaturated polyester resin) modified bitumen, respectively. On the temperature-dependent graphs of these values;

$$f(T) = f_\infty e^{\left(\frac{-DT_0}{T-T_0}\right)} \quad (4)$$

the VFT curves were formed as shown in FIG. 4 by applying the Vogel-Fulcher-Tamman (VFT) equation, which is given above.

As a result of the calculation of the slopes, the durability (ductility) for pure bitumen is obtained as 5.8, while the durability (ductility) for 5% Polyester Resin (isophthalic acid-based isophthalic unsaturated polyester resin) modified bitumen is obtained as 10.4. These results show, 5% Polyester Resin (isophthalic acid-based isophthalic unsaturated polyester resin) modified bitumen will become brittle at lower temperatures than of pure bitumen. That is, 5% Polyester resin modified bitumen can be used at lower temperatures.

The values of glass transition temperatures can be obtained directly from the temperature-dependent behavior of M" data at a certain frequency (usually 1 kHz). FIG. 5 shows a comparison of glass transition temperatures for pure bitumen and 5% Polyester Resin (isophthalic acid-based isophthalic unsaturated polyester resin) modified bitumen by investigating the temperature dependence of M" at a constant frequency of 1 kHz. In this study, it was concluded from the temperature dependency of M" values that the glass transition temperatures were −20° C. and −30° C., respectively, for pure bitumen and 5% Polyester Resin (isophthalic acid-based isophthalic unsaturated polyester resin) modified bitumen, respectively.

Thus, with a 5% polyester resin additive, a durable material that maintains its flexible structure even at lower temperatures was obtained. It was observed that, 5% Polyester resin modified bitumen can maintain its flexible structure at temperatures 10° C. lower compared to pure bitumen. Thus this result can be evaluated as, modified bitumen can be used in regions where night-day and seasonal temperature differences are high based on different parameters and sizes in 8 graphs.

In conclusion, in summary;

The desired result was obtained with the addition of 5% isophthalic acid-based isophthalic unsaturated polyester resin into 50-70 penetration bitumen to obtain more durable bitumen. While bitumen has a mechanically flexible structure at temperatures above the glass transition temperature, it has a brittle structure defined as glass state at temperatures below this temperature. Accordingly, while the glass transition temperature of pure bitumen was −20° C., the glass transition temperature was reduced to around −30° C. when 5% polyester resin was added to the bitumen. Thus, the structure will maintain its elasticity at lower temperatures. Another parameter that supports the situation related to glass transition temperatures is the durability (ductility) values obtained by the same methods. Durability is a measure of the material's resistance to mechanical stress.

Thus, modified bitumen has been made more durable for road pavements. The product is currently suitable for use in road pavement applications, especially for pavements in regions with low-high temperature differences.

Although there are studies in the literature examining the physical and mechanical properties of bituminous mixtures, there are no studies examining the dielectric properties and associating them with the structure. Regarding this issue, research on the examination of the dielectric properties of pure bitumen based on thickness was conducted by our study group and was accepted by an important journal on the subject.[49]

Pure bitumen was modified with Polyester Resin in the invention study. There is no such detailed research on modified bitumen obtained by the modification process, including both performance research and the examination of dielectric properties. In this study, both gap in the literature was filled and the glass transition temperature, which is extremely important in terms of use, and temperature-dependent dielectric properties of bitumen materials were determined.

The present study determines that the glass transition temperature of the modified bitumen obtained by adding 5% by mass Polyester Resin polymer to the 50/70 penetration pure bitumen material used in asphalt applications is lower than the glass transition temperature of the standard bitumen. In order to obtain this evaluation, the Cole-Cole equation and then processing of the Vogel-Fulcher-Tamman (VFT) equation from the data obtained as a result of Cole-Cole equation was used.

The evaluation method in the invention study is a method used for polymers and polymeric materials in the literature and used by us in several international articles recently.[50, 51,52]

It is determined that the addition of 5% Polyester Resin to the pure bitumen changes the glass transition temperature by approximately 10° C. with the help of this method. Thus, modified bitumen becomes more durable than pure bitumen. This doping and evaluation method used is considered to be the first for international asphalt examinations in line with the literature reviews. Moreover, the glass transition temperature of the bitumen sample structurally modified in a low-cost way through dielectric examinations can be detected in a short period, such as a few hours, with the present invention. In addition, the dielectric constant, dielectric loss, relaxation time, Cole-Cole curvature coefficient, AC conductivity values will also be determined, and studies will be paved the way to increase its durability by making forward-looking different contributions to the bitumen.

Bitumen with AC 50-70 penetration was provided as asphalt cement to be used in the study. Bitumen with 5% Polyester Resin was produced by adding orthophthalic polyester resin as a modifying additive.

Dielectric measurements of bitumen samples are defined by capacitive measurements of samples. Bitumen and modified bitumen samples were analyzed by placing bitumen samples between conductive electrodes, and measuring the samples formed into capacitors with parallel plates for this. The thicknesses (approximately 2.5 mm) of pure bitumen and 5% Polyester Resin modified bitumen were taken equally to see the effect of the modification. Capacities C and dielectric loss factor tan δ of the samples are measured by dielectric spectroscopy measurements. From capacity values, dielectric constant ε' is obtained with the following equation;

$$\varepsilon' = \frac{C * d}{\varepsilon_0 * A} \quad (1)$$

Here, d is the thickness of the capacitor, A is the surface area of the capacitor, and $\varepsilon_0$ is the electrical permittivity of vacuum. From ε' and tan values;

$$\varepsilon'' = \varepsilon' * \tan \delta \quad (2)$$

dielectric loss ε" is obtained with the help of the equation above. Dielectric loss is the measure of the energy loss that occurs as a result of the interaction of the electrically polarized charges with each other and the structure during polarization under the influence of the applied external electric field. The energy loss reaches maximum values when the charges are polarized well. Sometimes these values can be obtained directly from data, sometimes they can be determined by some experimental equations. Cole-Cole equations are also one of the equations used in these analyses.

$$\varepsilon^*(\omega) = \varepsilon_\infty \frac{\varepsilon_s - \varepsilon_\infty}{1 + (i\omega\tau_{CC})^\beta} \quad (3)$$

Figure 1:
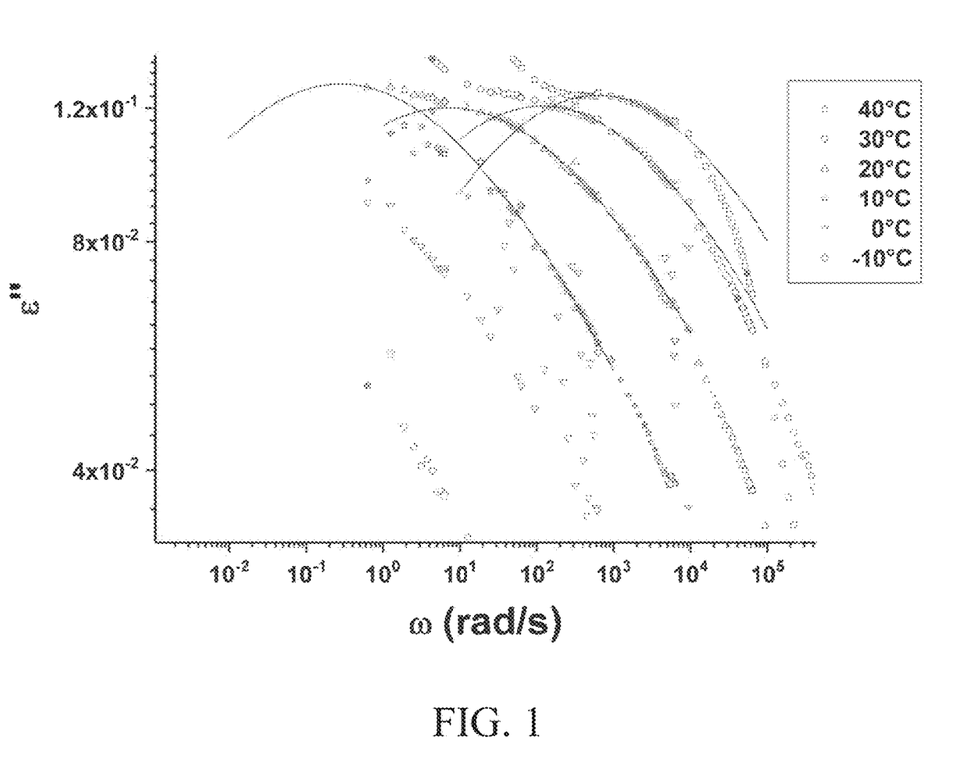
FIG. 1: Dependence of the dielectric loss ($\varepsilon''$) on the angular frequency and the Cole-Cole slopes for pure bitumen.
Figure 2:
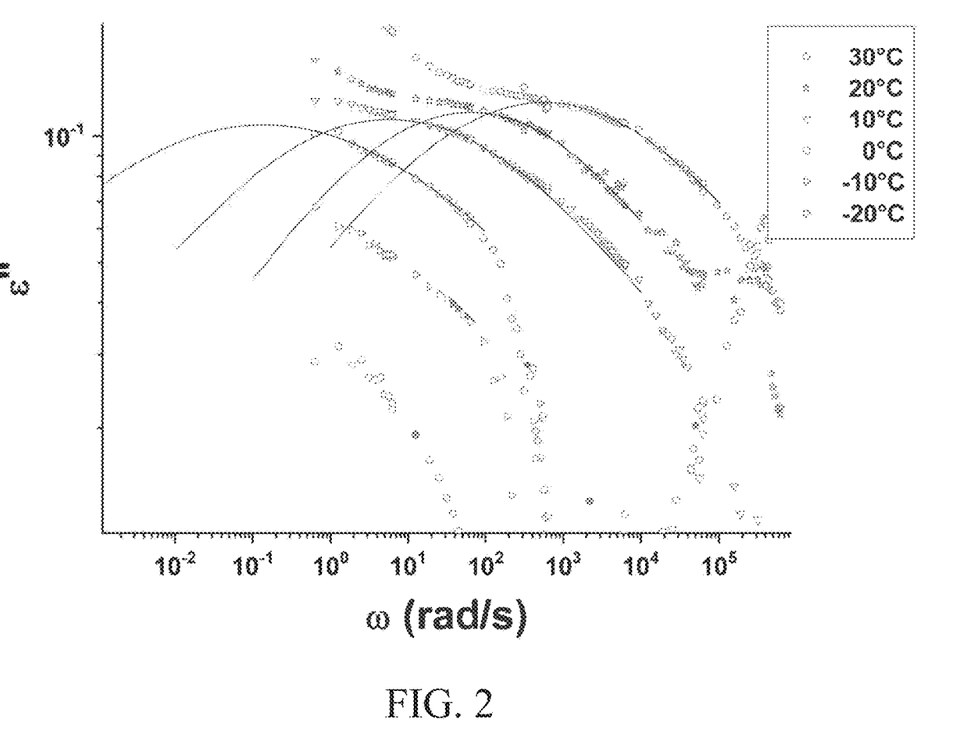
FIG. 2: Dependence of the dielectric loss ($\epsilon''$) on the angular frequency and the Cole-Cole slopes for 5% isophthalic acid-based isophthalic unsaturated polyester resin modified bitumen.

The relaxation time values of the polarization mechanism can be determined depending on this equation by considering the relevant frequencies at which maximum energy loss is observed. The angular frequency-dependent dielectric loss behavior of pure bitumen and 5% Polyester Resin modified bitumen, respectively, was examined in FIG. 1 and FIG. 2. With the help of the red Cole-Cole curves here, $\omega_{maximum\ \varepsilon''}$ values where the maximum energy loss was observed were obtained. When the temperature dependence of $\omega_{maximum\ \varepsilon''}$ values is examined, it is seen that there is no Arrhenius type behavior and that the behavior complies with the Vogel-Fulcher-Tamman (VFT) behavior, which is affected by the change in the viscosity observed in the dielectric properties of polymer and polymeric materials. Vogel-Fulcher-Tamman equation is given as follows;

$$f_{maximum\ \varepsilon''\ or\ maximum\ M''}(T) = f_\infty e^{\left(\frac{-DT_0}{T-T_0}\right)} \quad (4)$$

Following the angular frequency, the equation can be expressed as follows, based on the expression of ω=2πf, $$\omega_{maximum\ \varepsilon''\ or\ maximum\ M''}(T) = \omega_\infty e^{\left(\frac{-DT_0}{T-T_0}\right)}. \quad (5)$$

Figure 3:
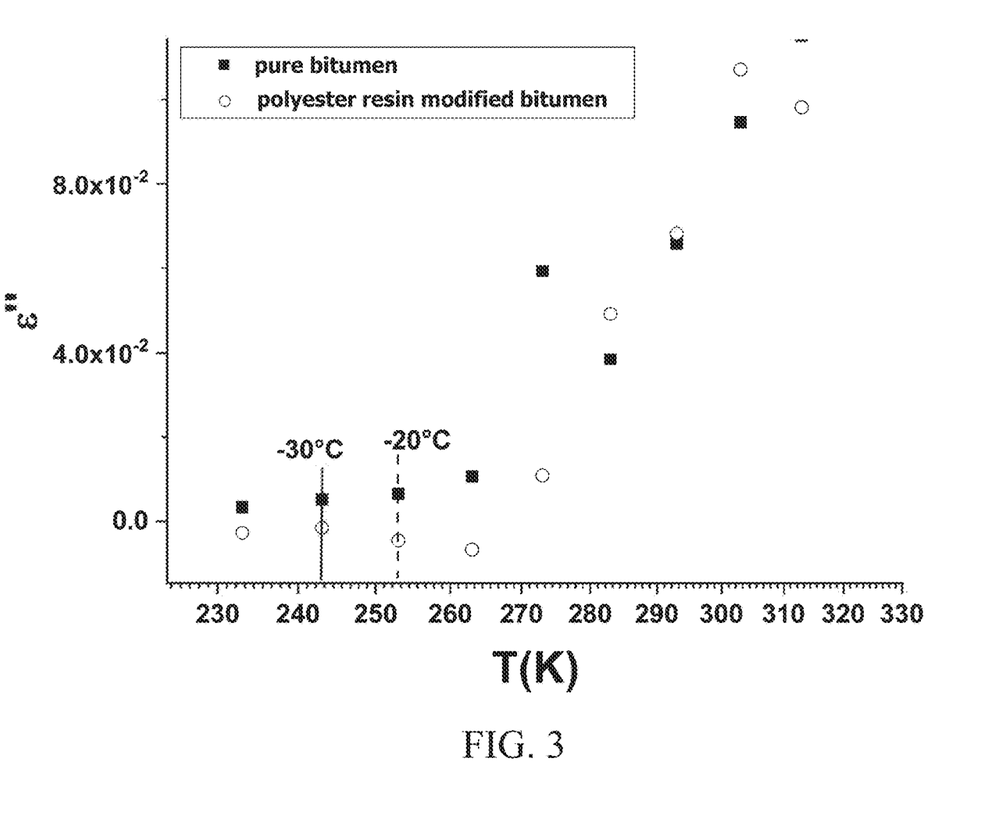
FIG. 3: Temperature dependence of the angular frequency values with maximum dielectric loss and the Vogel-Fulcher-Tamman (VFT) slopes for pure bitumen and 5% isophthalic acid-based isophthalic unsaturated polyester resin modified bitumen.

Here $\omega_\infty$ is the ω value of the VFT curve observed at very high temperatures. D is the measure of the brittleness of the structure undergoing glass transition. T is the temperature value in Kelvin and $T_0$ is the Vogel temperature in Kelvin. It is known from the literature that the Vogel temperature maybe 30-70 K lower than the glass transition temperatures obtained from calorimeters and direct temperature-dependent dielectric responses. This difference may be due to the type of material and the density of the void in it. FIG. 3 shows the VFT curves of temperature-dependent behavior of $\omega_{maximum\ \varepsilon''}$ angular frequencies for pure bitumen and 5% Polyester Resin modified bitumen. The Vogel temperature of pure bitumen is obtained as 232 K, while the Vogel temperature for 5% Polyester Resin modified bitumen is obtained as 215 K as a result of the calculation of the slopes. These results show that 5% Polyester Resin modified bitumen will become brittle at lower temperatures, that is, it can be used in road applications at lower temperatures than pure bitumen can be.

Another description of dielectric relaxation can be made with an electrical module equivalent to the modules called mechanical flexibility coefficients. The electrical module M" is calculated from the dielectric constant ε' and dielectric loss ε" data;

$$M'' = \frac{\varepsilon''}{\varepsilon'^2 + \varepsilon''^2} \quad (6)$$

with the equation above. The dependence of the M" data depending on angular frequency exhibits a behavior similar to the dependence of the dielectric loss on the angular frequency. In addition, the data M" have a structure free from electrode polarization, which is encountered from time to time in dielectric measurements. Electrode polarization obscures the actual behavior desired to be observed at low frequencies.

Therefore, it is possible to check the Vogel temperatures obtained in the dielectric loss data in a sense by using the M" data in the calculation of glass transition temperatures.

Figure 6:
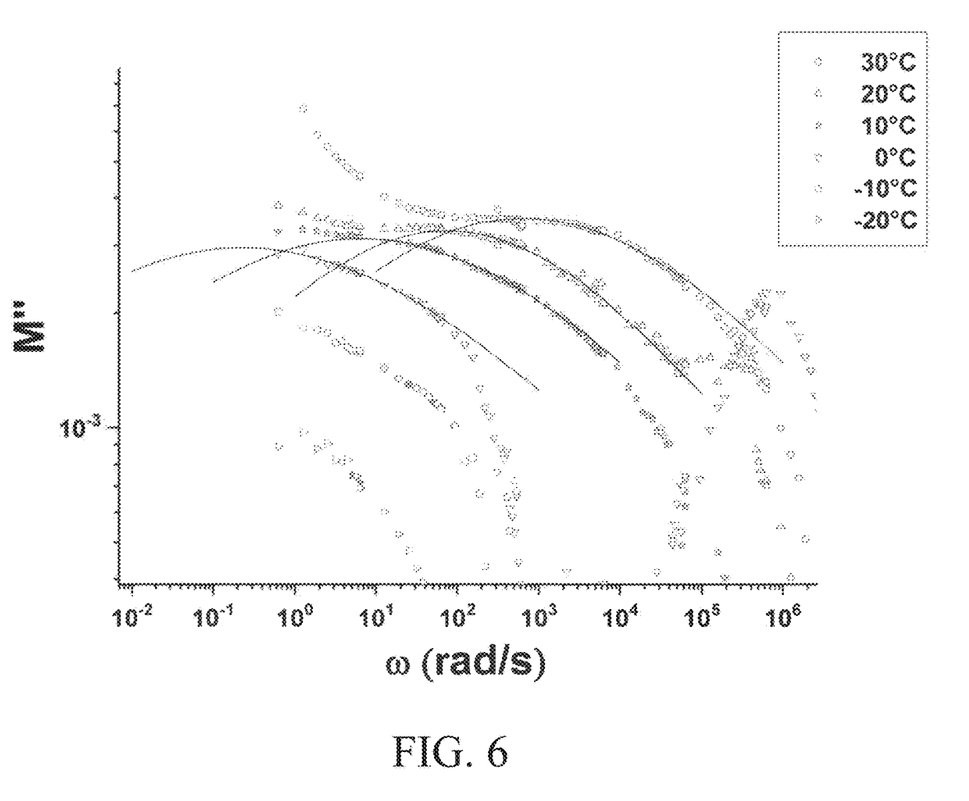
FIG. 6: Temperature dependence of the angular frequency values with maximum electrical modulus and the Vogel-Fulcher-Tamman (VFT) slopes for pure bitumen and 5% isophthalic acid-based isophthalic unsaturated polyester resin modified.
Figure 7:
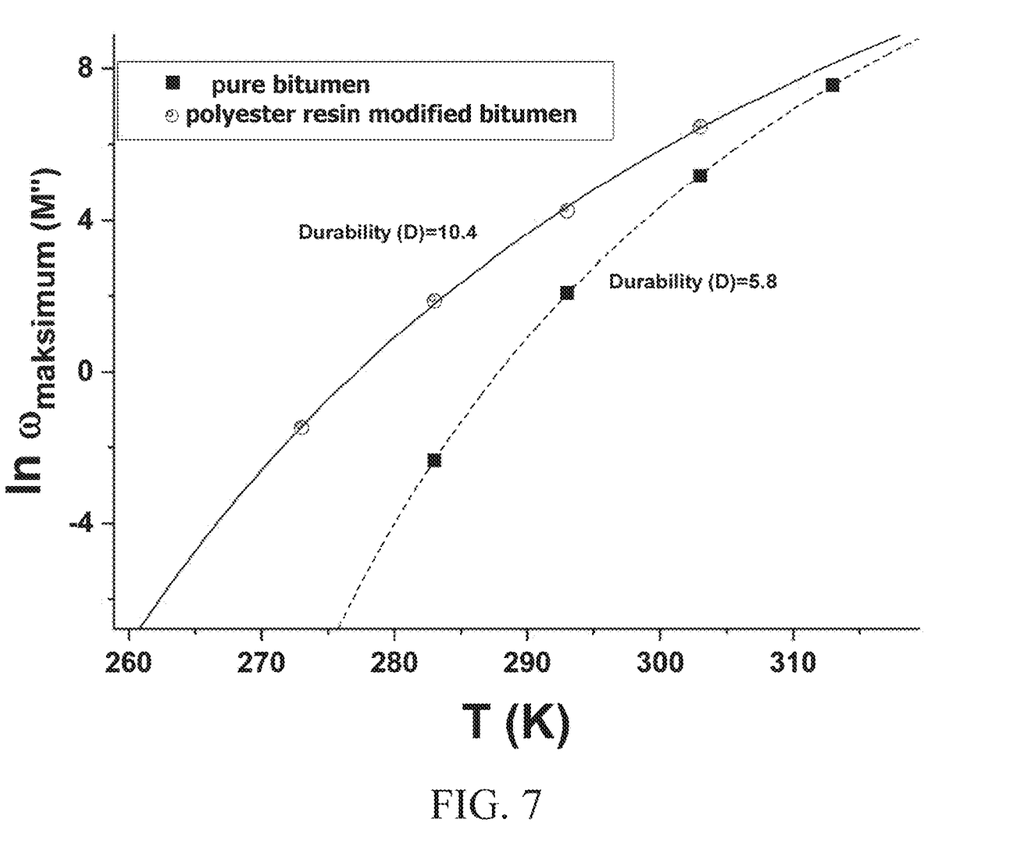
FIG. 7: Temperature dependence of the dielectric loss for pure bitumen and 5% isophthalic acid-based isophthalic unsaturated polyester resin modified bitumen.
Figure 8:
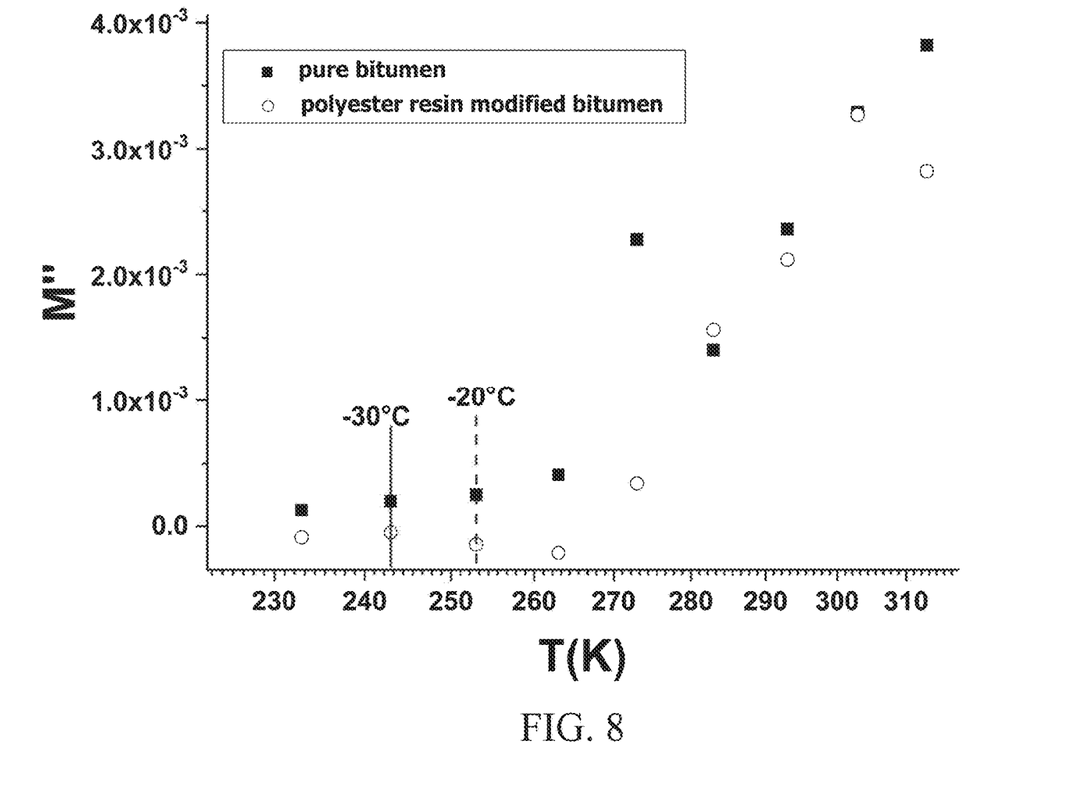
FIG. 8: Temperature dependence of the electrical module for pure bitumen and 5% isophthalic acid-based isophthalic unsaturated polyester resin modified bitumen.

FIG. 4 and FIG. 5 show the dependence of M" data on angular frequency for pure bitumen and 5% Polyester Resin modified bitumen, respectively. With the help of Cole-Cole curves, $\omega_{maximum\ M"}$ values were obtained in which maximum M" values were observed. The VFT curves were formed as shown in FIG. 6 by applying the VFT equation on the temperature-dependent graphs of these values. These curves gave 232 K and 198 K Vogel temperature values for pure bitumen and 5% Polyester Resin modified bitumen, respectively. The values were found to be compatible with the temperature values obtained from the dielectric loss data. The values of glass transition temperatures can be obtained directly from the temperature-dependent behavior of ε" and M" data at a certain frequency (usually 1 kHz). FIG. 7 and FIG. 8 show a comparison of glass transition temperatures for pure bitumen and 5% Polyester Resin modified bitumen through temperature-dependent behaviors of ε" and M" at a constant frequency of 1 kHz, respectively. In this study, it was concluded that the same data were obtained from the temperature dependence of ε" and M" values. The glass transition temperatures were 253 K (−20° C.) and 243 K (−30° C.) for pure bitumen and 5% Polyester Resin modified bitumen, respectively.

It was observed that bitumen modified with 5% Polyester Resin can still maintain its flexible structure at temperatures approximately 10° C. lower compared to pure bitumen and this modified bitumen can be used in regions where winter temperatures are very low due to high-temperature differences. In FIGS. 1-8, the results of this study were presented depending on different parameters and sizes.

Dielectric properties, which vary according to the type and properties of the material, can provide some clues about the design of bituminous pavements and be enabled to prevent the deterioration caused by various reasons (traffic loads, infrastructure problems, environmental impacts, etc.).

Important steps have been taken to investigate the physical, mechanical and chemical properties of the materials used in the field of engineering, as well as their electrical properties in recent years. Comprehensive answers can be obtained and provide convenience in solving different problems by evaluating the results that give the electrical properties of the materials in different study areas.[3-7]

Studies have shown that there is a connection between the deterioration problems occurring in the pavements and dielectric properties. One study found a good understanding of the dielectric history of bituminous pavements as a result of dielectric measurements of thousands of kilometers of old and new bituminous pavements over a decade. The results obtained in the study show that the dielectric value of the pavement increases rapidly within 5 years after the first year of construction, but gradually increases after 5 years. The rate of increase is directly related to traffic volume. The bond between the aggregate and the bitumen is first broken due to the water molecules within a few years before the cracking begins. A faster increase in dielectric value is observed when this is the case. The dielectric value decreases with the formation of cracks. This is seen as an increase in the air-filled gap ratio in the pavement due to the crack.[3]

It is possible to measure the quality of road pavements and to detect different types of deterioration by using dielectric properties.[3]

GPR device, one of the non-destructive test methods used in the field, is a very costly system for this although it provides an easy process. Therefore, the detection and evaluation of dielectric properties in the laboratory environment will be more advantageous in terms of cost. The dielectric spectroscopy method is based on examining the responses of a structure exposed to the variable electric field effect to the change of the field. Different dielectric constant and energy loss values will be found in different frequency regions depending on the type of possible polarization mechanisms in the structure. The behavior of dielectric properties depending on thickness, frequency of the applied electric field, and the temperature was determined for modified bitumen materials with different contents prepared in the study. The dielectric constant and energy loss values of the material were determined based on these values, and how the dielectric properties would change under different conditions and different material use was investigated and the optimum preparation conditions were determined. Polyester Resin was added as a modifying additive to pure bitumen in the study.

50-70 penetration bitumen heated at 160° C. was modified with the resin in the selected ratio and mixed at 500 rpm for at least 20 minutes until a homogeneous mixture was obtained during the preparation of the modified bitumen sample. Dielectric spectroscopy measurements were performed for the analysis of dielectric constant, dielectric loss, relaxation time, Cole-Cole curvature coefficient which is the measure of its spread in the frequency range, AC conductivity, glass transition temperature, and brittleness coefficient of the modified bitumen sample prepared after performance steps of mixing, cutting, and curing.

Dielectric spectroscopy measurements are performed under varying electric fields in the frequency range of 0.1 Hz to 20 MHz and in the temperature range of (−40° C. to 40° C.). The working principle of the measuring device is based on the Schering bridge and it is formed from a quadruple capacitor bridge in a closed system. Here, capacity and loss tangent values, which have an important place in many technological developments such as insulation and electronic circuits in the micro-electronics industry, are measured in the desired frequency and temperature range with the circuit to be formed by 3 capacitors with known capacity values and the material to be measured.[8-14]

However, the real (dielectric constant) and virtual (dielectric loss) values of the complex dielectric constant are obtained by the system. The fact that the system is compatible with the developing technology and isolated from factors such as noise etc. offers a great advantage to take healthy measurements of the samples. In addition, measurements can be taken with sufficient equipment in a wide range of sample catalogs from all types, i.e. from solid to liquid or from a hollow material to powder samples, with the impedance analyzer. Contributions are made in both the literature and the technological field by determining whether the sample developed is suitable for the intended use or the working conditions thereof thanks to these studies.

The frequency and temperature-dependent capacity and dielectric loss factor values of the samples were obtained from the dielectric measurements using a dielectric spectrometer. Capacity and loss factor values obtained were converted to dielectric constant values using the following general capacitance equation of dielectric materials $$\varepsilon' = \frac{Cd}{\varepsilon_0 A}. \tag{1}$$

Considering the ε as dielectric constant, "C" as capacitance, "d" as the thickness of the parallel plate capacitor here, the distance between the plates is "$\varepsilon_0$", the dielectric permissivity of the gap (8.85×10⁻¹² F/m), "A" is the surface area of the capacitor plates.[13-40]

In addition, dielectric loss from electrical loss factor (tan δ) values[16, 11-25, 27-37, 40, 42-45], $$\varepsilon'' = \varepsilon' \tan \delta \quad (7)$$

and AC conductivity values, $$\sigma' = \omega \varepsilon_0 \varepsilon'' \quad (8)$$

are derived using existing equations. ω is the angular frequency in the last equation. Not only the polarization mechanisms of the sample in the relevant frequency and temperature range can be observed by using the frequency and temperature dependence of the dielectric constant, but also the relaxation times of the observed polarization mechanisms will be calculated using the Cole-Cole experimental slope calculation.[44]

$$\varepsilon^*(\omega) = \varepsilon_\infty \frac{\varepsilon_s - \varepsilon_\infty}{1 + (i\omega\tau_{CC})^\beta} \quad (9)$$

Here, $\varepsilon^*(\omega)$ is a complex dielectric function, $\varepsilon_\infty$ is a dielectric constant at very high frequencies, $\varepsilon_s$ is a dielectric constant at very low frequencies, $\tau_{CC}$ is the relaxation time, β is a coefficient of distribution of relaxation in the frequency range, i.e. the curvature coefficient. (0<β<1)[46]

The shape of the slope of the Cole-Cole equation is similar to a ladder, the upper and lower parts of this ladder are regions independent of the applied frequency. The upper one from these regions extends to the low-frequency region, while the lower region extends to the higher frequencies. Dielectric constants values observed in these regions independent of frequency are defined as static dielectric constant and infinite high-frequency dielectric constant, respectively. It is predicted that a sample to which a variable electric field is applied will not be able to respond to the applied area at frequencies that can be defined as very low, that is, statically and at frequencies that we may not recognize as very high, that is, infinite, and therefore there will be no change in the net polarization of the structure. This situation is observed as the dielectric constant does not change at very low and very high frequencies.

These two dielectric constant values to be obtained from Cole-Cole slopes will allow us to find out the contribution of each polarization mechanism to total polarization. It will also be possible to determine the frequency ranges where each polarization mechanism is effective with Cole-Cole slopes. It may be possible to examine polarization on a microscopic scale even though the frequency ranges in which polarization mechanisms are effective are helpful factors in making evaluations about their types.

It will be determined which polarization types are dominant in which frequency regions in the structure by using the interpretations of dielectric constant and dielectric loss values. This determination will allow us to obtain results about how the charges move or displace in which frequency range in the structure. The frequency and temperature dependence of the dielectric constant and the dielectric loss will enable us to obtain information about the capacitive properties of the examined sample, that is, its performance as charge storage.

Dielectric spectroscopy is also used in structural examinations, especially in recent years, and structural features such as glass transition temperature and brittleness can also be detected using dielectric spectroscopy results.

$$\frac{1}{\tau} = Ae^{\left(\frac{-DT_0}{T-T_0}\right)} \quad (10)$$

Here τ is the relaxation time, A is the coefficient, D is the brittleness, T is the temperature and $T_0$ is the Vogel temperature.[47]

Since the samples we will examine will be in the polymer characteristic, they may be examples with significant glass transition temperatures, which are the transition temperatures from the flexible form to the brittle form. We will derive the dielectric magnitude, which is called the electrical module and is a measure of the electrical flexibility of the structure, from the dielectric constant and dielectric loss data and calculate the glass transition temperatures and brittleness by using temperature-dependent behavior of the electrical module, Vogel-Fulcher-Tamman slopes.

$$f(T) = f_\infty e^{\left(\frac{-DT_0}{T-T_0}\right)} \quad (11)$$

Where f is the frequency, $f_\infty$ is the frequency at infinitely high temperatures. AC conductivity data will be derived from dielectric loss data to determine how polarization, that is, charge mobility, occurs in the examined samples. The coefficient value used to determine the type of conductivity mechanism by using Jonsher slope from the frequency-dependent behavior of AC conductivity will be obtained and the temperature dependence of this coefficient will be examined and it will be determined which conductivity mechanism is dominant in which frequency region in the structure. In addition, the DC conductivity (independent of the frequency) value of the structure will be determined from the frequency-dependent behavior of AC conductivity and compared with the data obtained by DC measurements. By examining that to which frequency the behavior in the frequency-independent DC characteristic is observed, it will be determined to what extent the dipoles can contribute to the conductivity and to what extent the structure's conductivity level is.

TABLE 1

|  | Pure Bitumen | 5% Polyester modified Bitumen |
|---|---|---|
| T (Vogel) (obtained from dielectric loss ε" values) | 232K | 215K |
| Tg (obtained from dielectric loss ε" values) | 253K | 243K |
| T (Vogel) (obtained from electrical module loss component M" values) | 232K | 198K |
| Tg (obtained from electrical module loss component M" values) | 253K | 243K |
| Brittleness D (obtained from dielectric loss ε" values) | 1307 | 1628 |
| Brittleness D (obtained from electrical module loss component M" values) | 1580 | 2259 |

The glass transition temperature of the modified bitumen obtained by the modification process was reduced and its brittleness was increased and made more durable compared to pure bitumen, as can be seen in Table 1.

What is claimed is:

1. A determination of a dielectric loss, a glass transition temperature, and a brittleness of modified bitumen, comprising the following steps:
providing pure bitumen, wherein the pure bitumen is non-modified bitumen,
providing a polyester resin material for a modification of the pure bitumen,
selecting a temperature setting in a range of 160±10° C., by operating a drying oven to be used in a sample preparation process,
placing the non-modified bitumen in a solid or semi-solid form at room temperature, in the drying oven,
mixing a material by hand using a mixer, and then determining a surface temperature through a temperature measurement device, wherein the temperature measurement device is a thermometer,
taking the bitumen with a temperature being determined into a mixing unit of the mixer without losing the temperature of the bitumen, to be brought together with an additive material,
adding the polyester resin material stored at room temperature without contact with an air to the mixing unit in an amount corresponding to 5±0.1% of a bitumen weight,
continuing a mixing process until the additive material is evenly distributed over the bitumen used and becomes a homogeneous mixture,
filling a polyester resin modified bitumen sample into containers resistant to a first temperature of the polyester resin modified bitumen sample and keeping the polyester resin modified bitumen sample at room temperature,
cooling a modified bitumen material at room temperature for testing,
heating a modified mixture sample in the drying oven and making the modified mixture sample treatable to determine material properties by a dielectric spectroscopy method,
mixing the modified bitumen material again through a spatula before using the modified bitumen material,
laying the modified bitumen material on a non-stick surface by the spatula to make measurements on a dielectric spectrometer,
finally, producing bitumen as +5% isophthalic acid-based isophthalic unsaturated polyester resin,
determining values of a dielectric constant, the dielectric loss, a relaxation time, a Cole-Cole curvature coefficient being a measure of a spread in a frequency range, an AC conductivity, the glass transition temperature, and a brittleness coefficient of obtained modified bitumen by using dielectric spectroscopy measurements.

2. The determination of the dielectric loss, the glass transition temperature, and the brittleness of modified bitumen according to claim 1, wherein
in the step of laying the modified bitumen material on the non-stick surface by the spatula to make the measurements on the dielectric spectrometer,
the modified bitumen material is laid on the non-stick surface with different thicknesses of less than 5 mm and a diameter of 4 cm.

3. The determination of the dielectric loss, the glass transition temperature, and the brittleness of modified bitumen according to claim 1, wherein
in the step of placing the non-modified bitumen in the solid or semi-solid form at room temperature, in the drying oven,
the non-modified bitumen is kept in the drying oven until reaching a temperature of 160±10° C.

4. The determination of the dielectric loss, the glass transition temperature, and the brittleness of modified bitumen according to claim 3, wherein
after the step of adding the polyester resin material stored at room temperature without contacting with the air to the mixing unit in the amount corresponding to 5±0.1% of the bitumen weight,
the mixer is set to rotate at 500 rpm and operated to obtain a mixture at a temperature of 160° C.

5. The determination of the dielectric loss, the glass transition temperature, and the brittleness of modified bitumen according to claim 3, wherein
in the step of laying the modified bitumen material on the non-stick surface by the spatula to make the measurements on the dielectric spectrometer,
the modified bitumen material is laid on the non-stick surface with different thicknesses of less than 5 mm and a diameter of 4 cm.

6. The determination of the dielectric loss, the glass transition temperature, and the brittleness of modified bitumen according to claim 3, wherein
in the step of mixing the material by hand using the mixer, and then determining the surface temperature through the temperature measurement device,
the mixer used is in a non-deformable structure up to a temperature range of 160±10° C.

7. The determination of the dielectric loss, the glass transition temperature, and the brittleness of modified bitumen according to claim 6, wherein
after the step of adding the polyester resin material stored at room temperature without contacting with the air to the mixing unit in the amount corresponding to 5±0.1% of the bitumen weight,
the mixer is set to rotate at 500 rpm and operated to obtain a mixture at a temperature of 160° C.

8. The determination of the dielectric loss, the glass transition temperature, and the brittleness of modified bitumen according to claim 6, wherein
in the step of laying the modified bitumen material on the non-stick surface by the spatula to make the measurements on the dielectric spectrometer,
the modified bitumen material is laid on the non-stick surface with different thicknesses of less than 5 mm and a diameter of 4 cm.

9. The determination of the dielectric loss, the glass transition temperature, and the brittleness of modified bitumen according to claim 6, wherein
in the step of adding the polyester resin material stored at room temperature without contacting with the air to the mixing unit in the amount corresponding to 5±0.1% of the bitumen weight,
the polyester resin material is stored in a glass container.

10. The determination of the dielectric loss, the glass transition temperature, and the brittleness of modified bitumen according to claim 9, wherein
after the step of adding the polyester resin material stored at room temperature without contacting with the air to the mixing unit in the amount corresponding to 5±0.1% of the bitumen weight,
the mixer is set to rotate at 500 rpm and operated to obtain a mixture at a temperature of 160° C.

11. The determination of the dielectric loss, the glass transition temperature, and the brittleness of modified bitumen according to claim 9, wherein in the step of laying the modified bitumen material on the non-stick surface by the spatula to make the measurements on the dielectric spectrometer, the modified bitumen material is laid on the non-stick surface with different thicknesses of less than 5 mm and a diameter of 4 cm.

12. The determination of the dielectric loss, the glass transition temperature, and the brittleness of modified bitumen according to claim 1, wherein after the step of adding the polyester resin material stored at room temperature without contacting with the air to the mixing unit in the amount corresponding to 5±0.1% of the bitumen weight, the mixer is set to rotate at 500 rpm and operated to obtain a mixture at a temperature of 160° C.

13. The determination of the dielectric loss, the glass transition temperature, and the brittleness of modified bitumen according to claim 12, wherein in the step of laying the modified bitumen material on the non-stick surface by the spatula to make the measurements on the dielectric spectrometer, the modified bitumen material is laid on the non-stick surface with different thicknesses of less than 5 mm and a diameter of 4 cm.

* * * * *